United States Patent [19]

Katzen

[11] Patent Number: 5,002,568
[45] Date of Patent: Mar. 26, 1991

[54] INTRAOCULAR LENS

[75] Inventor: Leed S. Katzen, Baltimore, Md.

[73] Assignee: Surgidev Corporation, Goleta, Calif.

[21] Appl. No.: 144,335

[22] Filed: Jan. 15, 1988

Related U.S. Application Data

[63] Continuation of Ser. No. 915,535, Oct. 6, 1986, abandoned.
[51] Int. Cl.$^5$ .............................................. A61F 2/16
[52] U.S. Cl. ........................................................ 623/6
[58] Field of Search ........................................... 623/6

[56] References Cited

U.S. PATENT DOCUMENTS 4,846,832 7/1989 Wichterle ................................ 623/6

FOREIGN PATENT DOCUMENTS 2124500 2/1984 United Kingdom ..................... 623/6

Primary Examiner—Randall L. Green
Assistant Examiner—David H. Willse
Attorney, Agent, or Firm—Hugh D. Jaeger

[57] ABSTRACT

An intraocular lens for placement in a capsular bag, including a small hard inner lens optic and a soft pliable skirt surrounding the lens optic. The lens optic can be meniscus, bi-convex, plano convex, or the reverse lens optic. The lens optic is a high refractive index material and has a diameter of about 2–4 mm. The soft pliable skirt secures to an edge of the lens optic and extends away at a downwardly sloping angle. The outer diameter of the lens skirt can be up to 8–9 mm.

6 Claims, 2 Drawing Sheets

INTRAOCULAR LENS

This application is a continuation of U.S. Ser. No. 06/915,535, filed on Oct. 6, 1986, now abandoned.

BACKGROUND OF THE INVENTION

1. Field of the Invention

The present invention pertains to an intraocular lens and more particularly, pertains to an intraocular lens, with a hard optic and soft skirt, where the skirt is foldable allowing for insertion of the lens through a small incision in the eye.

2. Description of the Prior Art

The prior art has not demonstrated the aspects of a foldable lens including a hard optic. The foldable lenses of the prior art has usually been all silicone or other soft pliable material, which sometimes provides for distortion at the optical zone of the center of the lens.

The present invention overcomes the disadvantages of the prior art by providing a foldable lens with a hard optic of high refractive index material and a soft pliable skirt about the hard optic.

SUMMARY OF THE INVENTION

The general purpose of the present invention is to provide an intraocular lens which is intended for placement in the capsular bag and allows for insertion of the lens through a small incision in the eye. The lens is self centering and does not require any additional supporting structures. The lens optic can be meniscus, bi-convex or plano convex, and the skirt can also include an appropriate single or double barrier ridge.

According to one embodiment of the present invention, there is provided an intraocular lens for placement in a capsular bag, including a small hard inner lens optic and a soft pliable outer skirt surrounding the lens optic. The lens optic material can be PMMA, polysulfonce, polycarbonate, or like biocompatible material. The diameter is about 2-4 mm. The soft pliable skirt can be silicone, hydrogel, or a like material Which is biocompatible and secured to the edge of the lens optic. The diameter is about 8-9 mm. The skirt assumes a convex - concave cross-section and can include feet as well as a downwardly extending ridge, such as a double barrier ridge, or the like.

Significant aspects and features of the present invention include a lens which does not require any supporting structure and centers itself within the capsular bag.

Another significant aspect and feature of the present invention is a lens skirt which is foldable, allowing for insertion through a small incision in the eye, such as with a phaco operation.

Having thus described embodiments of the present invention, it is the principle object hereof to provide a intraocular lens with a hard non-foldable plastic center optic and a soft foldable skirt surrounding the center optic of the lens.

One object of the present invention is a lens which is self-centering within the capsular bag, and does not have any external mounted supporting structure.

DESCRIPTION OF PREFERRED EMBODIMENTS

Figure 1:
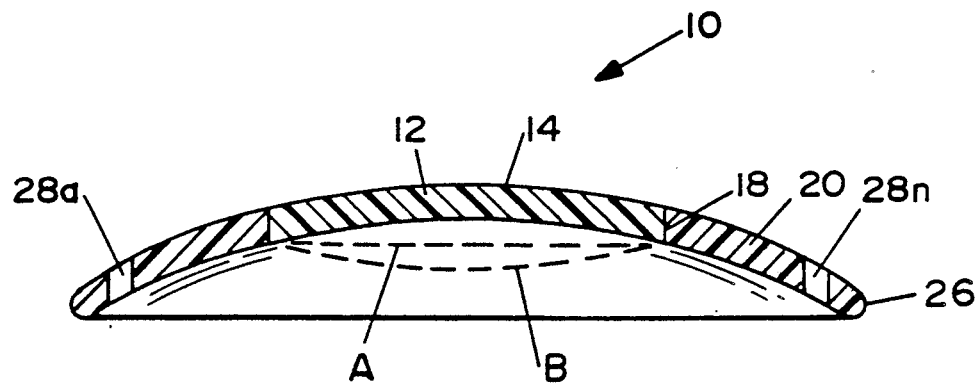
FIG. 1 illustrates a side view of an intraocular lens, the present invention.

FIG. 1 illustrates a side sectional view of an intraocular lens 10, the present invention, including a hard optic 12, and a soft skirt 20. The hard optic 12 is of a high refractive index material such as PMMA, polysulfone, polycarbonate, or the like, and is of a diameter of 2-4 mm. The lens optic can assume a meniscus, bi-convex, plano convex, or reverse optic configuration. A meniscus lens optic has been illustrated in FIG. 1, but of course, a plano convex configuration would follow dashed line "A" and a biconvex configuration would follow dashed line "B". The optic 12 of FIG. 1 includes a convex surface 14, a concave surface 16, and an edge 18. The skirt 20, has a curved convex - concave rim cross-section configuration and secures with adhesive, or the like, to the edge 18 of the optic 12. The thickness of the rim as well as the skirt can be 0.2 to 0.3 mm. The edge of the skirt 26, is slightly rounded. The skirt can be made of silicone, hydrogel, or other like biocompatible material and would have an outer diameter of 8-9 mm. The skirt can also be provided with positioning holes 28a-28n about the outer circumference of the skirt as so desired.

Figure 2:
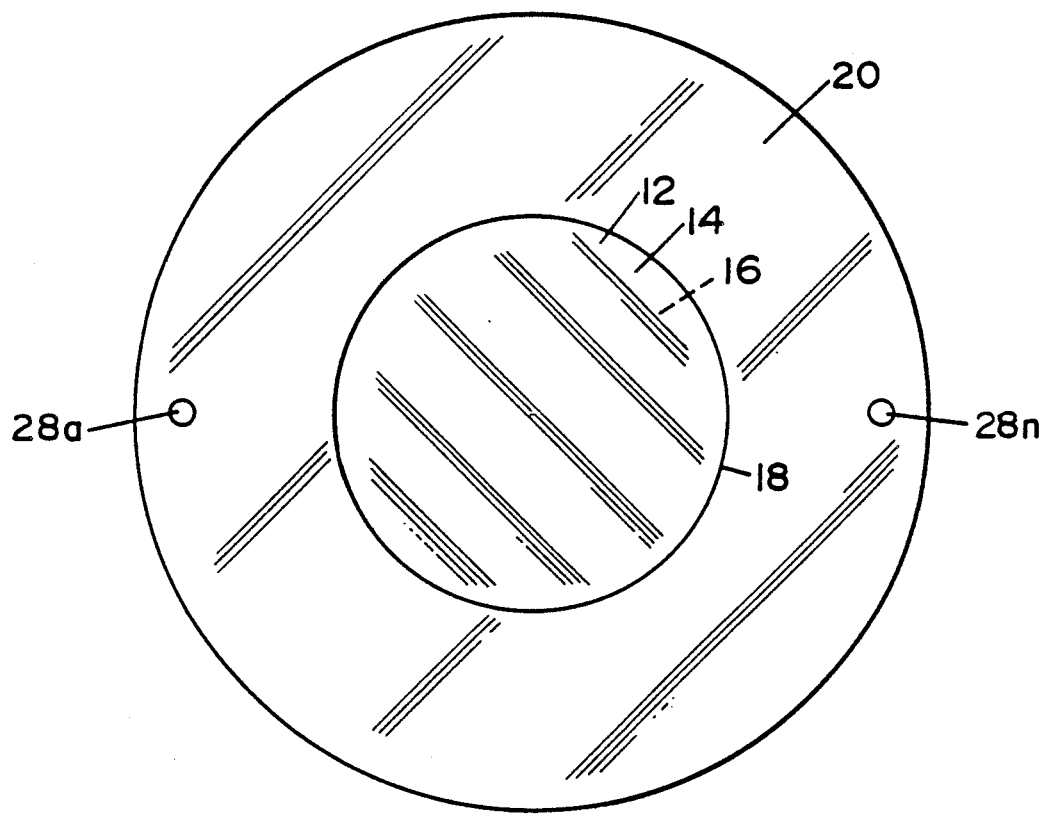
FIG. 2 illustrates a top view of FIG. 1.

FIG. 2 illustrates a top view of the intraocular lens 10, where all numerals correspond to those elements previously described.

FIRST ALTERNATIVE EMBODIMENT

Figure 3:
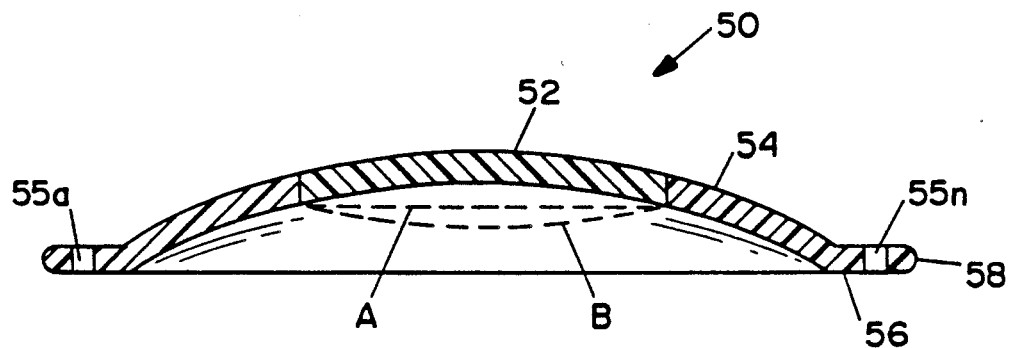
FIG. 3 illustrates an alternative embodiment of an intraocular lens.

FIG. 3 illustrates a cross-sectional view of an intraocular lens 50, the first alternative embodiment of the present invention. The lens includes a hard optic 52, a soft pliable skirt 54 with a surrounding rim 56, opposed to the rounded edge 26 of FIGS. 1 and 2. Positioning holes 55a-55n can be provided in the rim 56. The rim 56 is provided with a rounded edge 58. All other elements are those as previously described. The thickness of the rim as well as the skirt can be 0.2 to 0.3 mm.

SECOND ALTERNATIVE EMBODIMENT

Figure 4:
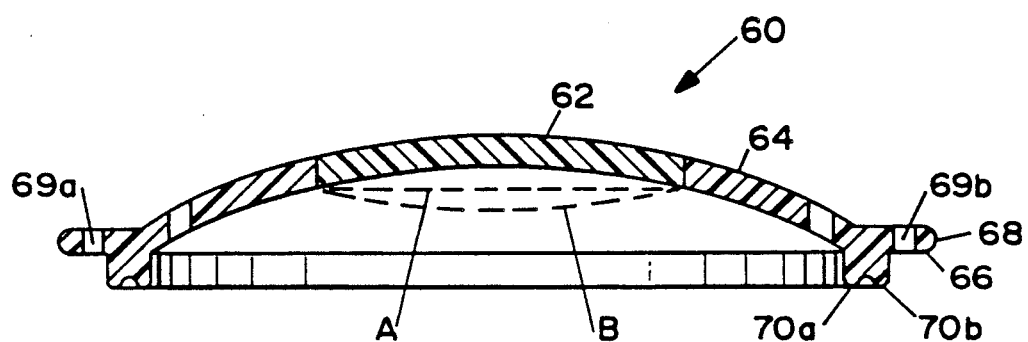
FIG. 4 illustrates another alterative embodiment of the present invention.

FIG. 4 illustrates a cross-sectional view of a intraocular lens 60, the second alternative embodiment, including a hard optic 62, a soft skirt 64, a rim 66 with a rounded edge 68. A double barrier ridge 70a and 70b extend downwardly from the junction of the skirt 64 and the rim 66. Positioning holes 69a and 69b can be provided in the rim 66. The double barrier ridge provides for the necessary YAG space.

MODE OF OPERATION

The lenses of FIGS. 1-4 provide that the skirt can be folded about the hard lens optic allowing for insertion of the lens in a small incision in the eye similar to that of a phaco operation. The hard optic, of course, is non-foldable, but the skirt is soft enough to be pliable. The skirt provides for placement in the capsular bag and is inherently self centering. The lens also has the advantage of having no loops which require subsequent placement.

FIG. 4 provides for a laser double barrier ridge which provides for YAG spacing.

Various modifications can be made to the present invention without departing from the apparent scope thereof.

I claim:

1. An intraocular lens comprising:
   a. a hard lens optic of high refractive index material;
   b. a soft skirt surrounding the edge of said lens optic and being of a foldable material, an anterior surface of the skirt and an anterior surface of the lens optic forming a continuous convex surface;
   c. said skirt including a rim extending radially outward from an edge of said skirt; and,
   d. ridge means extending downwardly from a junction of said skirt and said rim.

2. Lens of claim 1, wherein said material of said lens optic is selected from a group consisting of PMMA, polysulfone, polycarbonate, or like high refractive index polymer material.

3. Lens of claim 1, wherein said soft skirt is selected from a group consisting of silicone, hydrogel or like foldable material.

4. Lens of claim 1, wherein said hard lens optic is from 2 to 4 millimeters in diameter.

5. Lens of claim 1, wherein said skirt has an outer diameter of from 8 to 9 millimeters.

6. Lens of claim 1, wherein lens thickness is from 0.2 to 0.3 millimeters.

* * * * *